United States Patent
Deo et al.

(10) Patent No.: US 9,820,498 B2
(45) Date of Patent: *Nov. 21, 2017

(54) PROCESS FOR PREPARING AN AQUEOUS SOLUTION OF SACCHARIDES AND METHYLCELLULOSE

(71) Applicant: Dow Global Technologies LLC, Midland, MI (US)

(72) Inventors: Puspendu Deo, Midland, MI (US); Roland Adden, Bomlitz (DE); Matthias Knarr, Nienburg/Weser (DE); Robert L. Sammler, Midland, MI (US); Kathryn Brown, Mount Pleasant, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/771,932

(22) PCT Filed: Apr. 8, 2014

(86) PCT No.: PCT/US2014/033275
§ 371 (c)(1),
(2) Date: Sep. 1, 2015

(87) PCT Pub. No.: WO2014/168917
PCT Pub. Date: Oct. 16, 2014

(65) Prior Publication Data
US 2016/0015058 A1 Jan. 21, 2016

Related U.S. Application Data

(60) Provisional application No. 61/811,301, filed on Apr. 12, 2013.

(51) Int. Cl.
*A61K 31/717* (2006.01)
*A23L 1/0534* (2006.01)
*A23L 1/29* (2006.01)
*A23L 29/262* (2016.01)
*A23L 33/00* (2016.01)
*A23L 33/24* (2016.01)

(52) U.S. Cl.
CPC ........... *A23L 1/0534* (2013.01); *A23L 29/262* (2016.08); *A23L 33/24* (2016.08); *A23L 33/30* (2016.08); *A61K 31/717* (2013.01); *A23V 2002/00* (2013.01)

(58) Field of Classification Search
CPC ........ A61K 31/717; A23L 1/0534; A23L 1/29
USPC .................................................... 426/2, 573
See application file for complete search history.

(56) References Cited

U.S. PATENT DOCUMENTS

| 4,042,719 | A | 8/1977 | Zimmermann nee Ignacz et al. |
|---|---|---|---|
| 4,316,982 | A | 2/1982 | Holst et al. |
| 6,235,893 | B1 | 5/2001 | Reibert et al. |
| 9,216,191 | B2 * | 12/2015 | Adden ............... A61K 31/7004 |
| 2004/0242862 | A1 | 12/2004 | Hammes |
| 2005/0085571 | A1 * | 4/2005 | Georgiev ............... B65D 65/46 524/27 |
| 2011/0269711 | A1 | 11/2011 | Adden et al. |

FOREIGN PATENT DOCUMENTS

| EP | 0210917 A2 | 2/1987 |
|---|---|---|
| EP | 1141029 | 5/2003 |
| WO | 02041702 A2 | 5/2002 |
| WO | 2010117781 A1 | 10/2010 |
| WO | 2011139763 A1 | 11/2011 |
| WO | 2012173838 A1 | 12/2012 |
| WO | 2013059064 A1 | 4/2013 |

OTHER PUBLICATIONS

Deo et al (U.S. Appl. No. 14/771,891).*
Inventor Name Search Knarr.*
Inventor Name Search Sammler.*
Inventor Name Search Adden.*
Inventor Name Search Brown.*
Lindberg, et al., Distribution of Substituents in O-Ethyl-O-(2-Hydroxy-Ethyl)Cellulose, Carbohydrate Research, 176, (1988), pp. 137-144.
Ackman, Fundamental Groups in the Response of Flame Ionization Detectors to Oxygenated Aliphatic Hydrocarbons, Journal of Gas Chromatography, (1964), pp. 173-179.
Addison, Flame Ionization Detector Molar Responses for Methyl Esters of Some Polyfunctional Metabolic Acids, Journal of Gas Chromatography, 6, (1968), pp. 135-138.
Sweet, et al., Quantitative Analysis by Barious G.L.C. Response-Factor Theories for Partially Methylated and Partially Ethylated Alditol Acetates, Carbohydrate Research, 40, (1975), pp. 217-225.

* cited by examiner

*Primary Examiner* — Shaojia Anna Jiang
*Assistant Examiner* — Everett White

(57) ABSTRACT

An aqueous solution comprising (a) one or more mono-, di- and/or oligosaccharides and (b) a methylcellulose, wherein the methylcellulose has anhydroglucose units joined by 1-4 linkages wherein hydroxy groups of anhydroglucose units are substituted with methyl groups such that s23/s26 is 0.36 or less, is produced by i) mixing the methylcellulose with an aqueous liquid comprising one or more mono-, di- and/or oligosaccharides at a shear rate of at least 1000 s$^{-1}$ or ii) mixing one or more mono-, di- and/or oligosaccharides with the methylcellulose and/or an aqueous liquid before, simultaneously with or after mixing the methylcellulose with the aqueous liquid at a shear rate of at least 1000 s$^{-1}$.

11 Claims, No Drawings

PROCESS FOR PREPARING AN AQUEOUS SOLUTION OF SACCHARIDES AND METHYLCELLULOSE

FIELD

The present invention relates a process for preparing an aqueous solution which comprises (a) one or more mono-, di- and/or oligosaccharides and (b) a certain methylcellulose. The present invention further relates to aqueous solutions that are useful as food additives or as food replacement, for example in methods for inducing satiety.

INTRODUCTION

Conventionally, methylcellulose has been found to be very useful in a variety of applications, providing thickening, freeze/thaw stability, lubricity, moisture retention and release, film formation, texture, consistency, shape retention, emulsification, binding, gelation, and suspension properties. One unusual property of methylcellulose is that it is known to exhibit reverse thermal gelation in water, in other words, aqueous methylcellulose materials are soluble at cooler temperatures and gel at warmer temperatures. Most grades of methylcellulose gel at around 50 to 60° C.

A grade of methylcellulose that gels in water at a relatively low temperature, 38 to 44° C., is generally available under the trade name METHOCEL SG or SGA (The Dow Chemical Company). U.S. Pat. No. 6,235,893 teaches methylcelluloses that gel as low as 31° C. Methylcelluloses described in U.S. Pat. No. 6,235,893, when dissolved in water, have enhanced gel strength.

Specific grades of methylcellulose have been described that are useful for inducing satiety in an individual. International Patent Application WO2011/139763 discloses a cold aqueous medicament or food supplement, that when ingested and warmed by an individual, forms a gel mass in the individual's stomach, said gel mass consisting essentially of methylcellulose and water. The methylcellulose utilized in the Examples of WO2011/139763 has a gelation temperature of 28° C.

In nutritional terms, satiety is a complex response, involving both an individual's emotional and physical perception of whether or not they have ingested enough. Satiety can be observed as a reduction of appetite immediately following consumption, or as a reduction of food intake at the next meal. As can be appreciated, control of satiety is most relevant in cases where an individual consumes more calories than are necessary. Inducing satiety can be useful for causing a reduced caloric intake, i.e., for aesthetic purposes (i.e., as a slimming aid for weight loss or weight management) or for medical treatment (for example, for treating obesity). For purposes of this specification, "satiety" refers to a net reduction of caloric intake, or a robust reduction in hunger responses, by an individual. When satiety is induced by a specific grade of methylcellulose, it is often thought to arise at a sufficient gel fracture force $F_{GF}(37°\,C.)$. Accordingly, for this end-use a sufficient gel strength means a sufficient gel fracture force $F_{GF}(37°\,C.)$.

While the methylcelluloses described in WO2011/139763 and in U.S. Pat. No. 6,235,893 are very useful due to their low gelation temperatures in water, unfortunately they are difficult to fully hydrate, i.e., to bring them into aqueous solution with an ability to deliver sufficient gel fracture force when warmed to 37° C. As described in WO2011/139763, to obtain a 2% aqueous solution of a methylcellulose which has a gelation temperature of only 28° C. a corresponding amount of ground and dried methylcellulose is added to water at room temperature while stirring at 500 rpm, the blend is cooled to about 1.5° C. and the speed of the stirrer is reduced stepwise: 500 rpm for 15 min, then 400 rpm for 10 min, then 200 rpm for 10 min, and then 100 rpm for 5 h. The solution is then stored over night at about 0.5 to about 1° C. Unfortunately, such process takes unduly long and requires an undue amount of cooling. Methylcellulose that is commercially available under the trade name METHOCEL SG or SGA (The Dow Chemical Company) and that gels in water at somewhat higher temperatures, usually at 38 to 44° C., can be brought into aqueous solution at somewhat higher temperatures, e.g., at temperatures of up to 10° C., but also for this type of methylcellulose cooling is required and the process to bring the methylcellulose into aqueous solution also takes unduly long.

Accordingly, one object of the present invention is to provide a more efficient process for preparing an aqueous solution of a methylcellulose which has a low gelation temperature.

Moreover, it would be desirable to dissolve methylcelluloses which gel at an individual's body temperature in aqueous liquids which are accepted by consumers, such as yogurts, smoothies, drinks, shakes, fruit beverages, beverage shots, sports drinks, and other solutions. These liquids usually comprise one or more mono-, di- and/or oligosaccharides, often for organoleptic reasons, but unfortunately the presence of mono-, di- and/or oligosaccharides in the aqueous solution often makes the dissolution of the above-mentioned methylcelluloses even more difficult.

The co-pending International Patent Application PCT/US12/059713, filed 11 Oct. 2012, discloses an aqueous composition which comprises an above-mentioned methylcellulose and one or more mono-, di- and/or oligosaccharides. The aqueous composition has a reasonably high gel fracture force $F_{GF}(37°\,C.)$ after warming to an individual's normal body temperature. However, increasing the gel fracture force $F_{GF}(37°\,C.)$ or decreasing the concentration of the methylcellulose while still maintaining a reasonably high gel fracture force $F_{GF}(37°\,C.)$ is still desired for several end-uses.

It has been suggested by skilled artisans that addition of specific types of compounds to drinks can enhance suppression of hunger when the compounds form strong gastric gels after consumption of the drinks. Strong gels can be formed at a temperature of an individual's normal body temperature by including in food high concentrations, e.g, concentrations of 5 weight percent or more, of a gelling methylcellulose, but high concentrations of the gelling methylcellulose are not accepted by many consumers for organoleptic reasons, specifically the slightly slimy texture when the gelling methylcellulose is incorporated in food at high concentrations. Accordingly, there is still a need that i) the gel strength of an aqueous gelled composition comprising an above-mentioned methylcellulose and one or more mono-, di- and/or oligosaccharides can be increased without substantially increasing the concentration of the methylcellulose in the composition and/or that ii) the concentration of the methylcellulose in the composition can be decreased without substantially decreasing the gel fracture force $F_{GF}(37°\,C.)$ of the aqueous gelled composition.

SUMMARY

Surprisingly, it has been found that an aqueous solution which comprises (a) one or more mono-, di- and/or oligosaccharides and (b) a certain methylcellulose which has a low gelation temperature can be obtained in an efficient process such that a considerably higher gel fracture force $F_{GF}(37°$ C.) of the aqueous solution is achieved than in known processes.

Accordingly, one aspect of the present invention is a process for preparing an aqueous solution which comprises (a) one or more mono-, di- and/or oligosaccharides and (b) a methylcellulose, wherein the methylcellulose has anhydroglucose units joined by 1-4 linkages wherein hydroxy groups of anhydroglucose units are substituted with methyl groups such that s23/s26 is 0.36 or less, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups, wherein i) the methylcellulose is mixed with an aqueous liquid comprising one or more mono-, di- and/or oligosaccharides at a shear rate of at least 1000 $s^{-1}$ or wherein ii) one or more mono-, di- and/or oligosaccharides are mixed with the methylcellulose and/or an aqueous liquid before, simultaneously with or after mixing the methylcellulose with the aqueous liquid at a shear rate of at least 1000 $s^{-1}$.

Another aspect of the present invention is an aqueous solution which comprises (a) one or more mono-, di- and/or oligosaccharides and (b) an above-mentioned methylcellulose, wherein the concentration of the methylcellulose is from 0.2 to 2.5 weight percent and the aqueous solution has a gel fracture force $F_{GF}(37°$ C.) of i) at least 1.2 N when the concentration of the methylcellulose is from 0.2 to 0.4 weight percent, ii) at least 1.5 N when the concentration of the methylcellulose is from 0.5 to 0.7 weight percent, iii) at least 2.0 N when the concentration of the methylcellulose is from 0.8 to 1.0 weight percent, iv) at least 3.0 N when the concentration of the methylcellulose is from 1.1 to 1.3 weight percent, v) at least 4.5 N when the concentration of the methylcellulose is from 1.4 to 1.6 weight percent, vi) at least 6.5 N when the concentration of the methylcellulose is from 1.7 to 1.9 weight percent, vii) at least 8.5 N when the concentration of the methylcellulose is from 2.0 to 2.2 weight percent or viii) at least 12.0 N when the concentration of the methylcellulose is from 2.3 to 2.5 weight percent, based on the total weight of the aqueous solution.

Yet another aspect of the present invention is a medicament, food, food ingredient or food supplement which comprises or is made of the above-mentioned aqueous solution.

Yet aspect of the present invention is a method of reducing caloric intake, inducing satiety or reversibly reducing stomach void volume in an individual or of treating gastric ulcers, gastro-esophageal reflux disease, or obesity, or of aiding slimming, weight loss, or weight control in a non-obese individual, which comprises the step of administering to said individual the above-mentioned aqueous solution or the above-mentioned medicament, food, food ingredient or food supplement.

DESCRIPTION OF EMBODIMENTS

The process of the present invention relates to a high-shear process for preparing an aqueous solution of a methylcellulose. The aqueous solution of the methylcellulose may be liquid-like or solid-like. A cold liquid-like aqueous-solution form of the present invention, which has a temperature of about 0.5 to 10° C., transforms into its warm solid-like physical-gel form, as its temperature approaches body temperature (37° C.), and at body temperature it meets or exceeds the target gel fracture force $F_{GF}(37°$ C.) relevant to satiety applications as defined further below.

The methylcellulose used for preparing the aqueous solution of the present invention has anhydroglucose units joined by 1-4 linkages. Each anhydroglucose unit contains hydroxyl groups at the 2, 3, and 6 positions. Partial or complete substitution of these hydroxyls creates cellulose derivatives. For example, treatment of cellulosic fibers with caustic solution, followed by a methylating agent, yields cellulose ethers substituted with one or more methoxy groups. If not further substituted with other alkyls, this cellulose derivative is known as methylcellulose. An essential feature of the present invention is the use of a specific methylcellulose wherein hydroxy groups of anhydroglucose units are substituted with methyl groups such that s23/s26 is 0.36 or less, preferably 0.33 or less, more preferably 0.30 or less, most preferably 0.27 or less or 0.26 or less, and particularly 0.24 or less or 0.22 or less. Typically s23/s26 is 0.08 or more, 0.10 or more, 0.12 or more, 0.14 or more, or 0.16 or more.

In one embodiment of the invention hydroxy groups of anhydroglucose units are substituted with methyl groups such that the s23/s26 of the methylcellulose is 0.27 or less, preferably 0.26 or less, more preferably 0.24 or less or even 0.22 or less. In this embodiment of the invention s23/s26 of the methylcellulose typically is 0.08 or more, 0.10 or more, 0.12 or more, 0.14 or more, or 0.16 or more. The term "wherein hydroxy groups of anhydroglucose units are substituted with methyl groups" as used herein means that the hydrogen in a hydroxy group is replaced by a methyl group to form a methoxy group.

In another embodiment of the invention hydroxy groups of anhydroglucose units are substituted with methyl groups such that the s23/s26 of the methylcellulose is more than 0.27 and up to 0.36, preferably more than 0.27 and up to 0.33, and most preferably more than 0.27 and up to 0.30. In the ratio s23/s26, s23 is the molar fraction of anhydroglucose units wherein only the two hydroxy groups in the 2- and 3-positions of the anhydroglucose unit are substituted with methyl groups and s26 is the molar fraction of anhydroglucose units wherein only the two hydroxy groups in the 2- and 6-positions of the anhydroglucose unit are substituted with methyl groups. For determining the s23, the term "the molar fraction of anhydroglucose units wherein only the two hydroxy groups in the 2- and 3-positions of the anhydroglucose unit are substituted with methyl groups" means that the two hydroxy groups in the 2- and 3-positions are substituted with methyl groups and the 6-positions are unsubstituted hydroxy groups. For determining the s26, the term "the molar fraction of anhydroglucose units wherein only the two hydroxy groups in the 2- and 6-positions of the anhydroglucose unit are substituted with methyl groups" means that the two hydroxy groups in the 2- and 6-positions are substituted with methyl groups and the 3-positions are unsubstituted hydroxy groups.

Formula I below illustrates the numbering of the hydroxy groups in anhydroglucose units.

Formula I

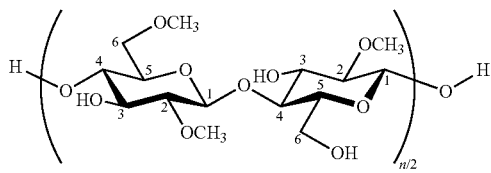

The methylcellulose preferably has a DS(methyl) of from 1.55 to 2.25, more preferably from 1.65 to 2.20, and most preferably from 1.70 to 2.10. The degree of the methyl substitution, DS(methyl), also designated as DS(methoxyl), of a methylcellulose is the average number of OH groups substituted with methyl groups per anhydroglucose unit.

The determination of the % methoxyl in methylcellulose (B) is carried out according to the United States Pharmacopeia (USP 34). The values obtained are % methoxyl. These are subsequently converted into degree of substitution (DS) for methyl substituents. Residual amounts of salt have been taken into account in the conversion.

The viscosity of the methylcellulose is preferably at least 50 mPa·s, more preferably at least 200 mPa·s, even more preferably at least 400 mPa·s or at least 500 mPa·s and most preferably at least 600 mPa·s or at least 700 mPa·s, when measured as a 2 wt.-% aqueous solution at 5° C. at a shear rate of 10 s$^{-1}$. The viscosity of the methylcellulose is preferably up to 30000 mPa·s, more preferably up to 10000 mPa·s, even more preferably up to 7000 mPa·s and most preferably up to 6000 mPa·s or up to 3000 mPa·s or up to 2000 mPa·s or even only up to 1500 mPa·s, when measured as indicated above.

One or more mono-, di- and/or oligosaccharides are another essential feature of the aqueous solution of the present invention or of the medicament, food, food ingredient or food supplement of the present invention. Useful monosaccharides have the elemental chemical formula $C_xH_{2x}O_x$, where x is at least 3, preferably from 3 to 7, more preferably 4, 5 or 6, and most preferably 6. Preferred monosaccharides are glucose and fructose. Useful disaccharides are, for example, lactose, maltose and sucrose. Sucrose, commonly also designated as saccharose, is preferred. Oligosaccharides have 3 to 10, preferably 3 to 7, monosaccharide units linked by glycosidic bonds. Examples of oligosaccharides are fructo-oligosaccharides, such as fructans, or galacto-oligosaccharides, or manno-oligosaccharides, or galactomanno-oligosaccharides, or gluco-oligosaccharides, such as maltodextrins or cyclodextrins or cellodextrins. The flowable or spoonable medicament, food, food ingredient or food supplement of the present invention can comprise more than one type of mono-, di- and/or oligosaccharides as component (a). The weight ranges and weight ratios relating to component (a) relate to the total weight of the mono-, di- and/or oligosaccharides. Preferred examples of component (a) are listed in the Council Directive 2001/111/EC of 20 Dec. 2001 relating to certain sugars intended for human consumption, as published in the Official Journal of the European Communities L 10/53, Dec. 1, 2002, such as semi-white sugar, (white) sugar, dried glucose syrup, dextrose, dextrose monohydrate, anhydrous dextrose or fructose. These sugars can be in solid or liquid form. Council Directive 2001/111/EC lists sugar solution, invert sugar solution, invert sugar syrup or glucose syrup. The sugar solution, invert sugar solution and invert sugar syrup are characterized by dry matter of not less than 62% by weight.

In the process for preparing an aqueous solution, the above described methylcellulose is typically utilized in ground and dried form. It is mixed with an aqueous liquid and one or more mono-, di- and/or oligosaccharides.

In one aspect of the present invention the methylcellulose is mixed with an aqueous liquid that comprises one or more mono-, di- and/or oligosaccharides at a shear rate of at least 1000 s$^{-1}$. Aqueous liquids that comprise one or more mono-, di- and/or oligosaccharides can be natural or man-made liquids, such as yogurts, smoothies, drinks, shakes, fruit beverages, beverage shots, sports drinks, and aqueous other solutions comprising one or more mono-, di- and/or oligosaccharides, as well as emulsions, including compositions for ice creams, creams, mousses, cream cheese, ketchup, spreads, dips, picante, salad dressing, homogenized milk, mayonnaise, gravies, puddings, soups, sauces, sport drinks and breakfast type cereal products such as porridge. The liquids are aqueous since they comprise a substantial amount of water. For purposes of this specification, "liquid" refers to any substance that takes the shape of its container at 10° C.

In another aspect of the present invention one or more mono-, di- and/or oligosaccharides are mixed with the methylcellulose and/or an aqueous liquid before, simultaneously with or after mixing the methylcellulose with the aqueous liquid at a shear rate of at least 1000 s$^{-1}$.

In both aspects of the present invention the methylcellulose is mixed with an aqueous liquid at a shear rate of at least 1000 s$^{-1}$, preferably at least 5000 s$^{-1}$, more preferably at least 10000 s$^{-1}$, even more preferably at least 15000 s$^{-1}$, and most preferably at least 25000 s$^{-1}$ or even at least 35000 s$^{-1}$. The shear rate is typically up to 150,000 s$^{-1}$, more typically up to 100,000 s$^{-1}$, even more typically up to 80000 s$^{-1}$, and most typically up to 60000 s$^{-1}$. Even higher shear rates can be applied, but they do not provide any additional advantages. The term "shear rate" is the commonly used term for the more specific term "shear strain rate".

The above-mentioned shear rate can be obtained in a high-shear device, such as a high-shear mixer, also known as rotor-stator mixer or homogenizer, high-shear mill or high-shear pump. A high-shear device commonly comprises a rotor in combination with a stationary part of the shear device, also referred to as "stationary", such as a stator or housing. The stationary creates a close-clearance gap between the rotor and itself and forms a high-shear zone for materials in this gap. The stationary can include single or multiple rows of openings, gaps or teeth to induce a kind of shear frequency and increased turbulent energy.

One metric for the degree or thoroughness of mixing is the shearing force generated by a mixing device with a high tip speed. Fluid undergoes shear when one area of fluid travels with a different velocity relative to an adjacent area. The tip speed of the rotor is a measure of the kinetic energy generated by the rotation according to the formula:

Tip speed=rotation rate of rotor×rotor circumference.

In the process of the present invention the rotation rate of the rotor is preferably at least 1000 rpm, more preferably at least 1200 rpm, even more preferably at least 1500 rpm, most preferably at least 2000 rpm, and particularly at least 4000 rpm. The rotation rate is generally up to 50,000 rpm, typically up to 40,000 rpm, more typically up to 30,000 rpm, and most typically up to 20,000 rpm or up to 10,000 rpm. Even higher rotation rates can be applied, but they do not provide any additional advantages.

The shear rate is based on the inverse relationship between the gap distance between the rotor and the stationary part of the shear device which is commonly referred to as the stator or housing. In the case the high-shear device is not equipped with a stator, the inner wall of a vessel serves as a stator.

Shear rate=Tip speed/gap distance between outer diameter of rotor and stationary.

In case the gap distance between the outer diameter of the rotor and the stationary is not constant over the entire size of the high-shear device, the smallest gap distance is determined.

The process of the present invention is preferably conducted in a shear device running at a tip speed of at least 2 m/s, preferably at least 4 m/s, more preferably at least 6 m/s, and most preferably at least 8 m/s. The tip speed is generally up to 100 m/s, typically up to 60 m/s, and more typically up to 40 m/s.

A further shearing is induced by a velocity difference between the tip velocity of the fluid at the outside diameter of the rotor and the velocity at the centre of the rotor.

High-shear devices are also called high-shear mixers and encompass different geometries such as colloid mills, toothed-devices, axial-discharge and radial-discharge rotor stator mixers (Atiemo-Obeng, V. A. and Calabrese, R. V., 2004. "Rotor-stator mixing devices" in Handbook of Industrial Mixing: Science and Practice, E. L. Paul, V. A. Atiemo-Obeng and S. M. Kresta, John Wiley & Sons, Hoboken, N.J., USA.). The high-shear device can be used in a continuous or batch operation.

It has surprisingly been found that by the process of the present invention aqueous solutions comprising (a) one or more mono-, di- and/or oligosaccharides and (b) an above-described methylcellulose are provided which after warming have considerably higher gel strength than when mixing the methylcellulose with an aqueous liquid in a low-shear process. The methylcellulose is generally mixed with an aqueous liquid while cooling the aqueous mixture to a temperature of not higher than 10° C., preferably not higher than 8° C., more preferably not higher than 6.5° C., and most preferably not higher than 5° C. Usually the aqueous mixture has a temperature of 0.5° C. to 2° C. When the aqueous mixture is cooled to the same temperature as in the prior art dissolution processes, such as disclosed in WO2011/139763, but a high-shear rate of at least 1000 $s^{-1}$, preferably at least 5000 $s^{-1}$, more preferably at least 10000 $s^{-1}$, even more preferably at least 15000 $s^{-1}$, and most preferably at least 25000 $s^{-1}$ or even at least 35000 $s^{-1}$ is applied, surprisingly an aqueous solution comprising (a) one or more mono-, di- and/or oligosaccharides and (b) an above-described methylcellulose is obtained which after warming has a considerably higher gel fracture force $F_{GF}(37°$ C.) than when applying a low-shear process as described in the prior art.

One or more mono-, di- and/or oligosaccharides can be mixed with the methylcellulose and/or an aqueous liquid before, simultaneously with or after mixing the methylcellulose with the aqueous liquid at a shear rate of at least 1000 $s^{-1}$. When the one or more mono-, di- and/or oligosaccharides are mixed with the methylcellulose or the aqueous liquid before or after mixing the methylcellulose with the aqueous liquid, the shear rate for mixing mono-, di- and/or oligosaccharide(s) with the methylcellulose or the aqueous liquid is not very critical. The mono-, di- and/or oligosaccharide(s) can be mixed with the methylcellulose or the aqueous liquid at a shear rate below 1000 $s^{-1}$, although preferably shear rates of at least 1000 $s^{-1}$, preferably at least 5000 $s^{-1}$, more preferably at least 10000 $s^{-1}$, even more preferably at least 15000 $s^{-1}$, and most preferably at least 25000 s or even at least 35000 $s^{-1}$ are applied. When the one or more mono-, di- and/or oligosaccharides are mixed with the methylcellulose or the aqueous liquid at the same time as the methylcellulose is mixed with the aqueous liquid, the one or more mono-, di- and/or oligosaccharides are of course also subjected to a shear rate of at least 1000 $s^{-1}$.

In one aspect of the process of the present invention one or more mono-, di- and/or oligosaccharides are present when the methylcellulose is mixed with an aqueous liquid at a shear rate of at least 1000 $s^{-1}$ or a preferred shear rate as described above. In this embodiment of the invention at least one mono-, di- and/or oligosaccharide has been or is mixed with the methylcellulose and/or an aqueous liquid before or simultaneously with mixing the methylcellulose with the aqueous liquid at a shear rate of at least 1000 $s^{-1}$. This embodiment of the invention is particularly useful for methylcelluloses wherein hydroxy groups of anhydroglucose units are substituted with methyl groups such that the s23/s26 of the methylcellulose is more than 0.27 and up to 0.36, preferably more than 0.27 and up to 0.33, and most preferably more than 0.27 and up to 0.30.

In another aspect of the process of the present invention one or more mono-, di- and/or oligosaccharides are only added to the aqueous solution of methylcellulose after having mixed the methylcellulose with the aqueous liquid at a shear rate of at least 1000 $s^{-1}$ or a preferred shear rate as described above. This embodiment of the invention is particularly useful for methylcelluloses wherein hydroxy groups of anhydroglucose units are substituted with methyl groups such that the s23/s26 of the methylcellulose is 0.27 or less, preferably 0.26 or less, more preferably 0.24 or less or even 0.22 or less. In this embodiment of the invention s23/s26 of the methylcellulose typically is 0.08 or more, 0.10 or more, 0.12 or more, 0.14 or more, or 0.16 or more.

The dissolution process of the present invention is completed in a much shorter time period that the process described in WO2011/139763. Usually the dissolution process of the present invention is completed in less than 30 minutes, typically in less than 15 minutes, more typically in less than 10 minutes, and most typically in 5 minutes or less.

The amount of the aqueous liquid is advantageously chosen for preparing the aqueous solution that the amount of the methylcellulose is from 0.2 to 2.5 weight percent, preferably from 0.5 to 2.2 weight percent, more preferably from 0.8 to 2.2 weight percent, and most preferably from 0.8 to 1.9 weight percent, based on the total weight of the aqueous solution. The amount of component (a), i.e., the total amount of one or more mono-, di- and/or oligosaccharides, preferably is from 1.0 to 30 weight percent, more preferably from 2.0 to 25 weight percent, most preferably from 4.0 to 20 weight percent, and particularly from 5.0 to 15 weight percent, based on the total weight of the liquid composition. The remaining portions are optional ingredients as described further below and liquid, such as water. The weight ratio w(a)/w(b), i.e., the weight ratio of (a) the total of one or more mono-, di- and/or oligosaccharides and (b) the methylcellulose, preferably is at least 1.0/1.0, more preferably at least 1.5/1.0 or at least 2.0/1.0 or at least 3.5/1.0 or at least 5.0/1.0. The weight ratio w(a)/w(b) is preferably up to 40:1.0, more preferably up to 30:1.0, most preferably up to 20:1.0, and particularly up to 15:1.0 or up to 10:1.0.

The major part of the aqueous liquid is water. Water may be mixed with a minor amount of one or more organic liquids which are preferably physiologically acceptable, such as ethanol, or one or more animal or vegetable oils, but the total amount of organic liquids is preferably not more than 20 percent, more preferably not more than 10 percent, even more preferably not more than 5 percent, based on the total weight of water and organic liquid. In one embodiment of the invention the aqueous liquid is not mixed with an organic liquid.

Optional ingredients may be added to the methylcellulose, to the mono-, di- and/or oligosaccharides, or the aqueous liquid before or during the high-shearing process described above. Alternatively, optional ingredients may be added after the preparation of the aqueous solution. The amount of the optional ingredients generally is not more than 20 percent, preferably not more than 10 percent, more preferably not more than 5 percent, and most preferably not more than 2 percent, based on the total amount of the aqueous solution comprising (a) one or more mono-, di- and/or oligosaccharides and (b) an above-mentioned methylcellulose. Examples of optional ingredients are artificial sweeteners, colorants, flavorants, antioxidants, preservatives, or combinations thereof. The sum of (a) one or more mono-, di- and/or oligosaccharides, (b) an above-mentioned methylcellulose, and (c) water is generally at least 70 percent, preferably at least 80 percent, more preferably at least 90, and most preferably at least 95 percent, based on the total weight of the aqueous solution.

In one embodiment of the invention the high-shear process described above provides an aqueous solution which comprises (a) one or more mono-, di- and/or oligosaccharides and (b) an above-mentioned methylcellulose, wherein the concentration of the methylcellulose is from 0.2 to 2.5, preferably from 0.5 to 2.2, more preferably from 0.8 to 2.2, even more preferably from 0.8 to 1.9, and most preferably from 1.0 to 1.9 weight percent, based on the total weight of the aqueous solution, and the aqueous solution has a gel fracture force $F_{GF}(37°\ C.)$ of i) at least 1.2 N, preferably at least 1.4 N, more preferably at least 1.8 N, and most preferably at least 2.2 N when the concentration of the methylcellulose is from 0.2 to 0.4 weight percent, or ii) at least 1.5 N, preferably at least 2.0 N, more preferably at least 2.5 N, and most preferably at least 3.0 N when the concentration of the methylcellulose is from 0.5 to 0.7 weight percent, or iii) at least 2.0 N, preferably at least 2.5 N, more preferably at least 3.0 N, and most preferably at least 3.5 N when the concentration of the methylcellulose is from 0.8 to 1.0 weight percent, or iv) at least 3.0 N, preferably at least 3.5 N, more preferably at least 4.5 N, and most preferably at least 5.0 N when the concentration of the methylcellulose is from 1.1 to 1.3 weight percent, or v) at least 4.5 N, preferably at least 5.0 N, more preferably at least 5.5 N and most preferably at least 6.0 N, when the concentration of the methylcellulose is from 1.4 to 1.6 weight percent, or vi) at least 6.5 N, preferably at least 7.5 N, more preferably at least 8.5 N and most preferably at least 10.0 N when the concentration of the methylcellulose is from 1.7 to 1.9 weight percent, or vii) at least 8.5 N, preferably at least 9.0 N, more preferably at least 10.0 N, and most preferably at least 11.0 N when the concentration of the methylcellulose is from 2.0 to 2.2 weight percent or viii) at least 12.0 N, preferably at least 13.0 N, more preferably at least 14.0 N, and most preferably at least 15.0 N when the concentration of the methylcellulose is from 2.3 to 2.5 weight percent, based on the total weight of the aqueous solution.

Mathematical rounding rules should be applied to the concentrations above. E.g., a concentration of 1.63 or 1.64 weight percent is to be understood as 1.6 weight percent, whereas a concentration of 1.65 or 1.66 weight percent is to be understood as 1.7 weight percent.

The term "wherein the aqueous solution has a gel fracture force $F_{GF}(37°\ C.)$ of . . . " as used herein means that the aqueous solution of the methylcellulose gels when it is warmed and after warming to 37° C. has the quoted gel fracture force $F_{GF}(37°\ C.)$.

Typically the gel fracture force $F_{GF}(37°\ C.)$ of such aqueous solution is up to 20 N, more typically up to 15 N when the concentration of the methylcellulose is up to 1.6 weight percent, based on the total weight of the aqueous solution. When the concentration of the methylcellulose is up to 2.5 weight percent, the gel fracture force $F_{GF}(37°\ C.)$ is typically up to 75 N, more typically up to 50 N.

The gel fracture force $F_{GF}(37°\ C.)$ is measured with a Texture Analyzer (model TA.XTPlus; Stable Micro Systems, 5-Kg load cell) at 37° C. Details of measuring the gel fracture force $F_{GF}(37°\ C.)$ are disclosed in the Examples. In vitro gel fracture force of the aqueous gelled solution which comprises (a) one or more mono-, di- and/or oligosaccharides and (b) an above-mentioned methylcellulose and which has a temperature of 37° C. is a proxy for in vivo gelling. It is quite surprising that due to the high-shear process of the present invention i) the gel fracture force $F_{GF}(37°\ C.)$ of the aqueous gelled solution can be increased without substantially increasing the concentration of the methylcellulose in the solution and/or that ii) the concentration of the methylcellulose in the solution can be decreased without substantially decreasing the gel fracture force $F_{GF}(37°\ C.)$ of the aqueous gelled solution. When the concentration of the methylcellulose described above is kept constant, the high-shear process described above enables the production of an aqueous solution which exhibits an increased gel strength (determined as gel fracture force) when the aqueous composition reaches the normal body temperature of an individual. Alternatively, the concentration of the methylcellulose described above in the aqueous solution can be decreased while still maintaining sufficiently high gel strength at the normal body temperature of an individual.

Another aspect of the present invention is a medicament, food, food ingredient or food supplement which comprises or is made of the above-mentioned aqueous solution of the present invention. Without wanting to be bound to the theory, applicants believe that the medicament, food, food ingredient or food supplement of the present invention generally forms a gel mass in the individual's stomach when the medicament, food, food ingredient or food supplement is ingested and warmed by an individual. This induces a feeling of satiety in an individual and often causes the individual to reduce its caloric intake.

It is contemplated that, in one embodiment, the medicament, food, food ingredient or food supplement is useful for indications that require gastric volume to be occupied for at least 60 minutes, preferably at least 120 minutes, more preferably at least 180 minutes, and most preferably at least 240 minutes.

In another embodiment, the medicament is useful for treating gastric ulcers, gastro-esophageal reflux disease, or obesity. In a preferred embodiment, the medicament is useful for treating obesity.

Alternatively, in another embodiment, the food, food ingredient or food supplement is useful as a slimming aid, weight loss aid, or weight control aid in a non-obese individual, for example for aesthetic reasons.

Alternatively, in another embodiment, the medicament, food, food ingredient or food supplement is useful for reducing caloric intake, for inducing satiety or for reversibly reducing stomach void volume in an individual.

Non-limiting examples of the medicament, food, food ingredient or food supplement of the present invention include yogurts, smoothies, drinks, shakes, fruit beverages, beverage shots, sports drinks, and other solutions, as well as emulsions, including ice creams, creams, mousses, cream cheese, ketchup, spreads, dips, picante, salad dressing, homogenized milk, mayonnaise, gravies, puddings, soups, sauces, sport drinks and breakfast type cereal products such as porridge.

Preferably the medicament, food, food ingredient or food supplement is a meal replacer or other food product intended to be used in a weight loss or weight control plan.

The present invention provides an effective and convenient method of providing good satiety effects to food compositions, especially those intended to be used in a weight loss or weight control plan. Furthermore, the products can be manufactured by conventional techniques and are economical to produce. Flavoring agents may be added to the medicament, food, food ingredient or food supplement, including varying types of cocoa, pure vanilla or artificial flavour, such as vanillin, ethyl vanillin, chocolate, malt, and mint, extracts or spices, such as cinnamon, nutmeg and ginger, and mixtures thereof. The edible compositions may comprise one or more conventional colourants, in conventional amounts as desired. The medicament, food, food ingredient or food supplement may comprise additional ingredients, such as added vitamins, added minerals, herbs, flavoring agents, antioxidants, preservatives or mixtures thereof.

The aqueous solution of the present invention or the medicament, food, food ingredient or food supplement comprising or being made of the aqueous solution of the present invention is preferably administered at least 45 minutes, more preferably at least 20 minutes, and most preferably, at least 15 minutes, before the individual eats. It is preferably administered up to 6 hours, more preferably up to 4 hours, and most preferably, up to 2 hours, before the individual eats.

It is understood that the individual's stomach eventually breaks down the gel mass, allowing it to pass from the stomach into the upper gastrointestinal tract. Naturally occurring mechanisms that break down the gel mass include physical disruption by stomach mobility and dilution with gastric juices (and consequent reversion to a liquid form). Degradation of gel mass occurs generally within 2 hours, preferably within 4 hours, and more preferably within 6 hours.

A method of making a methylcellulose used in the aqueous solution of the present invention is described in more detail in the Examples. Generally, cellulose pulp is treated with a caustic, for example an alkali metal hydroxide. Preferably, about 1.5 to about 3.0 mol NaOH per mol of anhydroglucose units in the cellulose is used. Uniform swelling and alkali distribution in the pulp is optionally controlled by mixing and agitation. The rate of addition of aqueous alkaline hydroxide is governed by the ability to cool the reactor during the exothermic alkalization reaction. In one embodiment, an organic solvent such as dimethyl ether is added to the reactor as a diluent and a coolant. Likewise, the headspace of the reactor is optionally purged with an inert gas (such as nitrogen) to minimize unwanted reactions with oxygen and molecular weight losses of the methylcellulose. In one embodiment, the temperature is maintained at or below 45° C.

A methylating agent, such as methyl chloride, is also added by conventional means to the cellulose pulp, either before, after, or concurrent with the caustic, generally in an amount of 2.0 to 3.5 mol methylating agent per mol of anhydroglucose units in the cellulose. Preferably, the methylating agent is added after the caustic. Once the cellulose has been mixed with caustic and methylating agent, the reaction temperature is increased to about 75° C. and reacted at this temperature for about half an hour.

In a preferred embodiment, a staged addition is used, i.e., a second amount of caustic is added to the mixture over at least 30 minutes, preferably at least 45 minutes, while maintaining the temperature at least at 55° C., preferably a least at 65° C. Preferably, 2 to 4 mol caustic per mol of anhydroglucose units in the cellulose is used. A staged second amount of methylating agent is added to the mixture, either before, after, or concurrent with the caustic, generally in an amount of 2 to 4.5 mol methylating agent per mol of anhydroglucose units in the cellulose. Preferably, the second amount of methylating agent is added prior to the second amount of caustic.

The methylcellulose is washed to remove salt and other reaction by-products. Any solvent in which salt is soluble may be employed, but water is preferred. The methylcellulose may be washed in the reactor, but is preferably washed in a separate washer located downstream of the reactor. Before or after washing, the methylcellulose may be stripped by exposure to steam to reduce residual organic content. The cellulose ether may subsequently be subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The methylcellulose is dried to a reduced moisture and volatile content of preferably 0.5 to 10.0 weight percent water and more preferably 0.8 to 5.0 weight percent water and volatiles based upon the weight of methylcellulose. The reduced moisture and volatile content enables the methylcellulose to be milled into particulate form. The methylcellulose is milled to particulates of desired size. If desired, drying and milling may be carried out simultaneously.

Some embodiments of the invention will now be described in detail in the following Examples.

EXAMPLES

Unless otherwise mentioned, all parts and percentages are by weight. In the Examples the following test procedures are used.

Production of Methylcellulose MC-I

Methylcellulose MC-I is produced according to the following procedure. Finely ground wood cellulose pulp is loaded into a jacketed, agitated reactor. The reactor is evacuated and purged with nitrogen to remove oxygen, and then evacuated again. The reaction is carried out in two stages. In the first stage, a 50 weight percent aqueous solution of sodium hydroxide is sprayed onto the cellulose until the level reaches 1.8 mol of sodium hydroxide per mol of anhydroglucose units of the cellulose, and then the temperature is adjusted to 40° C. After stirring the mixture of aqueous sodium hydroxide solution and cellulose for about 20 minutes at 40° C., 1.5 mol of dimethyl ether and 2.3 mol of methyl chloride per mol of anhydroglucose units are added to the reactor. The contents of the reactor are then heated in 60 min to 80° C. After having reached 80° C., the first stage reaction is allowed to proceed for 5 min. Then the reaction is cooled down to 65° C. in 20 min.

The second stage of the reaction is started by addition of methyl chloride in an amount of 3.4 molar equivalents of methyl chloride per mol of anhydroglucose unit. The addition time for methyl chloride is 20 min. Then a 50 weight percent aqueous solution of sodium hydroxide at an amount of 2.9 mol of sodium hydroxide per mol of anhydroglucose units is added over a time period of 45 min. The rate of addition is 0.064 mol of sodium hydroxide per mol of anhydroglucose units per minute. After the second-stage addition is completed the contents of the reactor are heated up to 80° C. in 20 min and then kept at a temperature of 80° C. for 120 min.

After the reaction, the reactor is vented and cooled down to about 50° C. The contents of the reactor are removed and transferred to a tank containing hot water. The crude MC-I is then neutralized with formic acid and washed chloride free with hot water (assessed by AgNO3 flocculation test), cooled to room temperature and dried at 55° C. in an air-swept drier, and subsequently ground.

The methylcellulose MC-I has a DS(methyl) of 1.88 (30.9 wt. % methoxyl), a mol fraction (26-Me) of 0.3276±0.0039, a mol fraction (23-Me) of 0.0642±0.0060, an s23/s26 of 0.20±0.02, a steady-shear-flow viscosity $\eta(5° C., 10 s^{-1}, 2$ wt. % MC) of 5500 mPa·s, and a gelation temperature of 28° C. The properties of the methylcellulose MC-I are measured as described below.

Determination of the DS(methyl) of Methylcellulose

The determination of the % methoxyl in methylcellulose is carried out according to the United States Pharmacopeia (USP34). The values obtained are % methoxyl. These are subsequently converted into degree of substitution (DS) for methyl substituents. Residual amounts of salt are taken into account in the conversion.

Determination of the Gelation Temperature of Aqueous Methylcellulose

Aqueous methycellulose solutions are subjected to small-amplitude oscillatory shear flow (frequency=2 Hz, strain amplitude=0.5%) while warming from 5 to 85° C. at 1 K/min in a rotational rheometer (Anton Paar, MCR 501, Peltier temperature-control system). The oscillatory shear flow is applied to the sample placed between parallel-plate fixtures (type PP-50; 50-mm diameter, 1-mm separation [gap]). Water loss to the sheared material is minimized during the temperature ramp by (1) covering the fixtures with a metal ring (inner diameter of 65 mm, width of 5 mm, and height of 15 mm) and (2) placing a water-immiscible paraffin oil around the sample perimeter. The storage modulus G', which is obtained from the oscillation measurements, represents the elastic properties of the solution (during the gelation process of methylcellulose, G' increases). The loss modulus G", which is obtained from the oscillation measurements, represents the viscous properties of the solution. The low strain amplitude is in the linear viscoelastic regime to ensure that the applied shear flow does not create or destroy structure in the aqueous methylcellulose materials. The gelation temperature, $T_{gel}$, is identified as the temperature when G' and G" are equal (e.g. $T_{gel}=T(G'=G")$).

Determination of the Viscosity of Aqueous Methylcellulose

The steady-shear-flow viscosity $\eta(5° C., 10 s^{-1}, 2$ wt. % MC) of an aqueous 2-wt. % methylcellulose solution is measured at 5° C. at a shear rate of $10 s^{-1}$ with an Anton Paar Physica MCR 501 rheometer and cone-and-plate sample fixtures (CP-50/1, 50-mm diameters).

Determination of the Gel Fracture Force $F_{GF}(37° C.)$ of a Methylcellulose

Cylindrically-shaped gels (height=20 mm, diameter=20 mm) are fabricated by introducing about 6.5 g of an aqueous solution of methylcellulose having a temperature of about 5° C. into a syringe (20-mL volume, NORM-JECT Luer, one end cut off above the needle port), sealing the cut end with glass, and placing the syringe in a constant-temperature water bath (set at 39.5° C.) for one hour.

The gel fracture force $F_{GF}(37° C.)$ is measured with a Texture Analyzer (model TA.XTPlus; Stable Micro Systems, 5-Kg load cell) located inside a cabinet (model XT/TCH Stable Micro Systems, Surrey, UK) designed to hold the temperature at 37.0° C. The cylindrically-shaped gels are compressed between two plates (50-mm-diameter, plate compression rate=10 mm/s, trigger force=0.5 g, maximum distance=18 mm) within about two to three minutes after removal from the 39.5° C. water bath. The plate displacement [mm] and compression force [N] is measured at selected time intervals (400 points/s) until the gel collapses. The maximum compressional force, measured prior to the gel collapse, is identified as $F_{GF}(37° C.)$. The results of six replicates are typically averaged and the average results reported in units of Newton.

Determination of s23/s26 of Methylcellulose

The approach to measure the ether substituents in methylcellulose is generally known. See for example the approach described in principle for Ethyl Hydroxyethyl Cellulose in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 was conducted as follows: 10-12 mg of the methylcellulose were dissolved in 4.0 mL of dry analytical-grade dimethyl sulfoxide (DMSO) (Merck, Darmstadt, Germany, stored over 0.3 nm molecular sieve beads) at about 90° C. with stirring and then cooled to room temperature. The solution was stirred at room temperature over night to ensure complete solubilization/dissolution. The entire perethylation including the solubilization of the methylcellulose was performed using a dry nitrogen atmosphere in a 4 mL screw cap vial. After solubilization, the dissolved methylcellulose was transferred to a 22-mL screw-cap vial to begin the perethylation process. Powdered sodium hydroxide (freshly pestled, analytical grade, Merck, Darmstadt, Germany) and ethyl iodide (for synthesis, stabilized with silver, Merck-Schuchardt, Hohenbrunn, Germany) were introduced in a thirty-fold molar excess relative to the level of anhydroglucose units in the methylcellulose, and the mixture was vigorously stirred under nitrogen in the dark for three days at ambient temperature. The perethylation was repeated with addition of the threefold amount of the reagents sodium hydroxide and ethyl iodide compared to the first reagent addition, and stirring at room temperature was continued for an additional two days. Optionally, the reaction mixture could be diluted with up to 1.5 mL DMSO to ensure good mixing during the course of the reaction. Next, five mL of 5% aqueous sodium thiosulfate solution was poured into the reaction mixture, and the mixture was then extracted three times with 4 mL of dichloromethane. The combined extracts were washed three times with 2 mL of water. The organic phase was dried with anhydrous sodium sulfate (about 1 g). After filtration, the solvent was removed with a gentle stream of nitrogen, and the sample was stored at 4° C. until needed.

Hydrolysis of about 5 mg of the perethylated samples was performed under nitrogen in a 2-mL screw-cap vial with 1 mL of 90% aqueous formic acid under stirring at 100° C. for 1 hour. The acid was removed in a stream of nitrogen at 35-40° C. and the hydrolysis was repeated with 1 mL of 2M aqueous trifluoroacetic acid for 3 hours at 120° C. in an inert nitrogen atmosphere with stirring. After completion, the acid was removed to dryness in a stream of nitrogen at ambient temperature using ca. 1 mL of toluene for co-distillation.

The residues of the hydrolysis were reduced with 0.5 mL of 0.5-M sodium borodeuteride in 2N aqueous ammonia solution (freshly prepared) for 3 hours at room temperature with stirring. The excess reagent was destroyed by dropwise addition of about 200 µL of concentrated acetic acid. The resulting solution is evaporated to dryness in a stream of nitrogen at about 35-40° C. and subsequently dried in vacuum for 15 min at room temperature. The viscous residue was dissolved in 0.5 mL of 15% acetic acid in methanol and evaporated to dryness at room temperature. This was done five times and repeated four additional times with pure methanol. After the final evaporation, the sample was dried in vacuum overnight at room temperature.

The residue of the reduction was acetylated with 600 µL of acetic anhydride and 150 µL of pyridine for 3 hrs at 90° C. After cooling, the sample vial was filled with toluene and evaporated to dryness in a stream of nitrogen at room temperature. The residue was dissolved in 4 mL of dichloromethane and poured into 2 mL of water and extracted with 2 mL of dichloromethane. The extraction was repeated three times. The combined extracts were washed three times with 4 mL of water and dried with anhydrous sodium sulfate. The dried dichloromethane extract was subsequently submitted to GC analysis. Depending on the sensitivity of the GC system, a further dilution of the extract could be necessary.

Gas-liquid (GLC) chromatographic analyses were performed with Agilent 6890N type of gas chromatographs (Agilent Technologies GmbH, 71034 Boeblingen, Germany) equipped with Agilent J&W capillary columns (30 m, 0.25-mm ID, 0.25 µm phase layer thickness) operated with 1.5-bar helium carrier gas. The gas chromatograph was programmed with a temperature profile that held constant at 60° C. for 1 min, heated up at a rate of 20° C./min to 200° C., heated further up with a rate of 4° C./min to 250° C., and heated further up with a rate of 20° C./min to 310° C. where it was held constant for another 10 min. The injector temperature was set to 280° C. and the temperature of the flame ionization detector (FID) was set to 300° C. Exactly 1 µL of each sample was injected in the splitless mode at 0.5-min valve time. Data were acquired and processed with a LabSystems Atlas work station.

Quantitative monomer composition data were obtained from the peak areas measured by GLC with FID detection. Molar responses of the monomers were calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN Increments Used for ECN Calculations:

| Type of carbon atom | ECN increment |
|---|---|
| hydrocarbon | 100 |
| primary alcohol | 55 |
| secondary alcohol | 45 |

In order to correct for the different molar responses of the monomers, the peak areas were multiplied by molar response factors MRFmonomer which are defined as the response relative to the 2,3,6-Me monomer. The 2,3,6-Me monomer were chosen as reference since it was present in all samples analyzed in the determination of s23/s26.

MRFmonomer=ECN2,3,6-Me/ECNmonomer

The mol fractions of the monomers were calculated by dividing the corrected peak areas by the total corrected peak area according to the following formulas:

(1) s23 is the sum of the molar fractions of anhydroglucose units which meet the following condition [the two hydroxy groups in the 2- and 3-positions of the anhydroglucose unit are substituted with methyl groups, and the 6-position is not substituted (=23-Me)]; and (2) s26 is the sum of the molar fractions of anhydroglucose units which meet the following condition [the two hydroxy groups in the 2- and 6-positions of the anhydroglucose unit are substituted with methyl groups, and the 3-position is not substituted (=26-Me)].

Example 1

An aqueous solution of the methylcellulose MC-I and sucrose was prepared by adding 1.5 weight percent of the dry methylcellulose powder to an aqueous solution of sucrose which had an initial temperature of 25° C. to achieve a good dispersion using a Yamato LT 400 lab overhead mixer having a rotor diameter of 63.5 mm and a gap distance between the outer diameter of the rotor and the stationary of 10.16 mm and running at 500 rpm, which resulted in a shear rate of 164 $s^{-1}$. The concentration of the sucrose is listed in Table 1 below. The concentrations of sucrose and of the methylcellulose MC-I are based on the total weight of the aqueous solution. The mixture of the methylcellulose MC-I, the sucrose and the water was cooled to 2° C. within 20 minutes while stirring at the same speed. After the mixture of the methylcellulose MC-I, the sucrose and the water reached the temperature of 2° C., the mixture was subjected to high shear using a Silverson L4-R high-shear mixer (rotor stator) running at 5000 rpm resulting in a shear rate of 56070 $s^{-1}$ for 5 minutes. The Silverson L4-R high-shear mixer was equipped with a square hole high shear screen, and had a rotor diameter of 38.1 mm and a gap of 0.178 mm. For comparative purposes an aqueous solution of 1.5 wt. % of methylcellulose MC-I in water in the absence of sucrose was prepared in the same manner.

The gel fracture force $F_{GF}$(37° C.) was measured immediately after the preparation of the aqueous solution and was also measured after storage of the aqueous solution for 1 day at 4° C.).

Comparative Example A

An aqueous solution of the methylcellulose MC-I and sucrose was prepared by adding 1.5 weight percent of the dry methylcellulose powder to an aqueous solution of sucrose. The concentration of the sucrose is listed in Table 1 below. The concentrations of sucrose and of the methylcellulose MC-I are based on the total weight of the aqueous solution. The aqueous solution was substantially prepared as described in WO2011/139763. The dried methylcellulose powder was added to the aqueous solution of sucrose which had an initial temperature of 25° C. to achieve a good dispersion using a Yamato LT 400 lab overhead mixer having a rotor diameter of 63.5 mm and a gap distance between the outer diameter of the propeller and the stationary of 10.16 mm and running initially at 500 rpm. The speed of the stirrer was reduced stepwise: 500 rpm for 15 min, then 400 rpm for 10 min, then 200 rpm for 10 min while the blend was cooled to 2° C., and then 100 rpm for 6 h using the same overhead mixer described above. Stirring at 500 rpm resulted in a shear rate of 164 s$^{-1}$. The solution was then stored over night at 2° C. without stirring. For comparative purposes an aqueous solution of 1.5 wt. % of methylcellulose MC-I in water in the absence of sucrose was prepared in the same manner. The gel fracture force $F_{GF}$(37° C.) was subsequently measured as described above.

Aqueous solutions were produced comprising 1.5 weight percent of the methylcellulose MC-I and 0, 2.0, 5.0, 10.0 or 15.0 weight percent of sucrose, based on the total weight of the aqueous solution, according to the processes of Example 1 and Comparative Example A. The gel fracture forces $F_{GF}$(37° C.) are listed in Table 1 below.

TABLE 1

| Sucrose concentration, wt. % | Process of Comparative Example A, Average $F_{GF}$ (37° C.), N | Process of Example 1, Average $F_{GF}$(37° C.), N | |
|---|---|---|---|
| | | Immediately after preparation of the aqueous solution | After 1 day storage at 4° C. |
| 0 | 2.0 | 6.1 | 6.2 |
| 2.0 | 2.8 | 8.8 | 8.6 |
| 5.0 | 2.2 | 8.4 | 8.5 |
| 10.0 | 1.3 | 7.8 | 8.0 |
| 15.0 | 0.7 | 6.1 | 6.0 |

The results in Table 1 illustrate that the process of the present invention provides an aqueous solution which comprises (a) one or more mono-, di- and/or oligosaccharides and (b) an above-mentioned methylcellulose of much higher gel strength than when preparing a corresponding aqueous solution in a known low-shear process as disclosed in WO2011/139763, even when in both processes components (a) and (b) are in the same concentration and the mixture is cooled to the same temperature before warming the solution to 37° C. to measure the gel fracture forces $F_{GF}$(37° C.).

Example 2 and Comparative Example B

The procedures of Example 1 and of Comparative Example A were repeated, except that aqueous solutions were produced comprising a concentration of the methylcellulose MC-I as listed in Table 2 below and 15.0 weight percent of sucrose, based on the total weight of the aqueous solution. The gel fracture forces $F_{GF}$(37° C.) are listed in Table 2 below.

TABLE 2

| MC-I concentration, % | Process of Comparative Example B, $F_{GF}$(37° C.) | Process of Example 2, $F_{GF}$(37° C.), measured immediately after preparation of the aqueous solution |
|---|---|---|
| 1.0 | — | 3.5 N |
| 1.2 | — | 4.3 N |
| 1.5 | 0.7 N | 6.1 N |
| 1.8 | 1.4 N | 8.0 N |
| 2.0 | 1.9 N | 10.0 N |
| 2.1 | 2.7 N | 11.6 N |

The invention claimed is:
1. An aqueous solution comprising
   (a) one or more mono-, di- and/or oligosaccharides and
   (b) a methylcellulose, wherein the methylcellulose has anhydroglucose units joined by 1-4 linkages wherein hydroxy groups of anhydroglucose units are substituted with methyl groups such that s23/s26 is 0.36 or less, wherein s23 is the molar fraction of anhydroglucose units wherein only the two hydroxy groups in the 2- and 3-positions of the anhydroglucose unit are substituted with methyl groups and s26 is the molar fraction of anhydroglucose units wherein only the two hydroxy groups in the 2- and 6-positions of the anhydroglucose unit are substituted with methyl groups,
   wherein the concentration of the methylcellulose (MC) is from 0.2 to 2.5 percent and the aqueous solution has a gel fracture force $F_{GF}$(37° C.) of
   i) at least 1.2 N and up to 20 N when the MC concentration is from 0.2 to 0.4 percent,
   ii) at least 1.5 N and up to 20 N when the MC concentration is from 0.5 to 0.7 percent,
   iii) at least 2.0 N and up to 20 N when the MC concentration is from 0.8 to 1.0 percent,
   iv) at least 3.0 N and up to 20 N when the MC concentration is from 1.1 to 1.3 percent,
   v) at least 4.5 N and up to 20 N when the MC concentration is from 1.4 to 1.6 percent,
   vi) at least 6.5 N and up to 75 N when the MC concentration is from 1.7 to 1.9 percent,
   vii) at least 8.5 N and up to 75 N when the MC concentration is from 2.0 to 2.2 percent, or
   viii) at least 12.0 N and up to 75 N when the MC concentration is from 2.3 to 2.5 percent,
   based on the total weight of the aqueous solution.
2. The aqueous solution of claim 1 wherein the concentration of the methylcellulose (MC) is from 0.8 to 2.2 percent and the aqueous solution has a gel fracture force $F_{GF}$(37° C.) of
   at least 2.0 N and up to 20 N when the MC concentration is from 0.8 to 1.0 percent,
   at least 3.0 N and up to 20 N when the MC concentration is from 1.1 to 1.3 percent,
   at least 4.5 N and up to 20 N when the MC concentration is from 1.4 to 1.6 percent,
   at least 6.5 N and up to 75 N when the MC concentration is from 1.7 to 1.9 percent, or
   at least 8.5 N and up to 75 N when the MC concentration is from 2.0 to 2.2 percent,
   based on the total weight of the aqueous solution.
3. The aqueous solution of claim 1 wherein the concentration of the methylcellulose (MC) is from 0.8 to 2.2 percent and the aqueous solution has a gel fracture force $F_{GF}$(37° C.) of at least 3.0 N and up to 20 N when the MC concentration is from 0.8 to 1.0 percent, at least 4.5 N and up to 20 N when the MC concentration is from 1.1 to 1.3 percent, at least 5.5 N and up to 20 N when the MC concentration is from 1.4 to 1.6 percent, at least 8.5 N and up to 75 N when the MC concentration is from 1.7 to 1.9 percent, or at least 10.0 N and up to 75 N when the MC concentration is from 2.0 to 2.2 percent, based on the total weight of the aqueous solution.

4. The aqueous solution of claim 1 wherein the aqueous solution has been prepared by
   i) mixing the methylcellulose with an aqueous liquid comprising one or more mono-, di- and/or oligosaccharides at a shear rate of at least 1000 $s^{-1}$, or
   ii) mixing one or more mono-, di- and/or oligosaccharides with the methylcellulose and/or an aqueous liquid before, simultaneously with or after mixing the methylcellulose with the aqueous liquid at a shear rate of at least 1000 $s^{-1}$.

5. The aqueous solution of claim 1 wherein the viscosity of the methylcellulose is from 200 to 10000 mPa·s, when measured as a 2 wt. % solution in water at 5° C. at a shear rate of 10 $s^{-1}$.

6. The aqueous solution of claim 1 comprising from 2.0 to 25 percent of one or more mono-, di- and/or oligosaccharides, based on the total weight of the solution.

7. A medicament, food, food ingredient or food supplement comprising or being made of the aqueous solution of claim 1.

8. A method of reducing caloric intake, inducing satiety or reversibly reducing stomach void volume in an individual or of treating gastric ulcers, gastro-esophageal reflux disease, or obesity, or of aiding slimming, weight loss, or weight control in a non-obese individual, comprising the step of administering to said individual the medicament, food, food ingredient or food supplement of claim 7.

9. The method of claim 8, wherein the individual is not obese.

10. A method of reducing caloric intake, inducing satiety or reversibly reducing stomach void volume in an individual or of treating gastric ulcers, gastro-esophageal reflux disease, or obesity, or of aiding slimming, weight loss, or weight control in a non-obese individual, comprising the step of administering to said individual the aqueous solution of claim 1.

11. The method of claim 10, wherein the individual is not obese.

* * * * *